(12) United States Patent
Van Egmond et al.

(10) Patent No.: US 7,038,102 B2
(45) Date of Patent: May 2, 2006

(54) LIQUID CONTACTING OF POST-QUENCH EFFLUENT VAPOR STREAMS FROM OXYGENATE TO OLEFINS CONVERSION TO CAPTURE CATALYST FINES

(75) Inventors: Cor F. Van Egmond, Pasadena, TX (US); Zhong Yi Ding, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 328 days.

(21) Appl. No.: 10/629,963

(22) Filed: Jul. 30, 2003

(65) Prior Publication Data

US 2005/0027152 A1 Feb. 3, 2005

(51) Int. Cl.
*C07C 1/00* (2006.01)
*C07C 7/00* (2006.01)

(52) U.S. Cl. .................. 585/640; 585/639; 585/809

(58) Field of Classification Search ............. 585/639, 585/640, 809
See application file for complete search history.

(56) References Cited

U.S. PATENT DOCUMENTS

| | | | |
|---|---|---|---|
| 5,234,578 A | 8/1993 | Stine et al. | 208/113 |
| 6,121,504 A | 9/2000 | Kuechler et al. | 585/640 |
| 6,403,854 B1 | 6/2002 | Miller et al. | 585/638 |
| 6,459,009 B1 | 10/2002 | Miller et al. | 585/809 |
| 6,870,072 B1 * | 3/2005 | Lumgair et al. | 585/639 |

FOREIGN PATENT DOCUMENTS

| | | |
|---|---|---|
| WO | WO 2004/018387 | 4/2004 |
| WO | WO 2004/029009 | 8/2004 |

* cited by examiner

*Primary Examiner*—Walter D. Griffin
*Assistant Examiner*—In Suk Bullock

(57) ABSTRACT

A process is provided for converting oxygenate to olefins from a fluidized bed reactor which comprises removal of catalyst fines from a quenched vaporous effluent by contacting with a liquid low in catalyst fines content, e.g., oxygenate feedstock, or by-product water from the oxygenates to olefins conversion which is stripped and/or filtered. The process typically comprises: contacting a feedstock comprising oxygenate with a catalyst comprising a molecular sieve under conditions effective to produce a deactivated catalyst having carbonaceous deposits and a product comprising the olefins; separating the deactivated catalyst from the product to provide a separated vaporous product which contains catalyst fines; quenching the separated vaporous product with a liquid medium containing water and catalyst fines, in an amount sufficient for forming a light product fraction comprising light olefins and catalyst fines and a heavy product fraction comprising water, heavier hydrocarbons and catalyst fines; treating the light product fraction by contacting with a liquid substantially free of catalyst fines to provide a light product fraction having reduced catalyst fines content and a liquid fraction of increased fines content; compressing the light product fraction having reduced catalyst fines content; and recovering the light olefins from the compressed light product fraction.

31 Claims, 1 Drawing Sheet

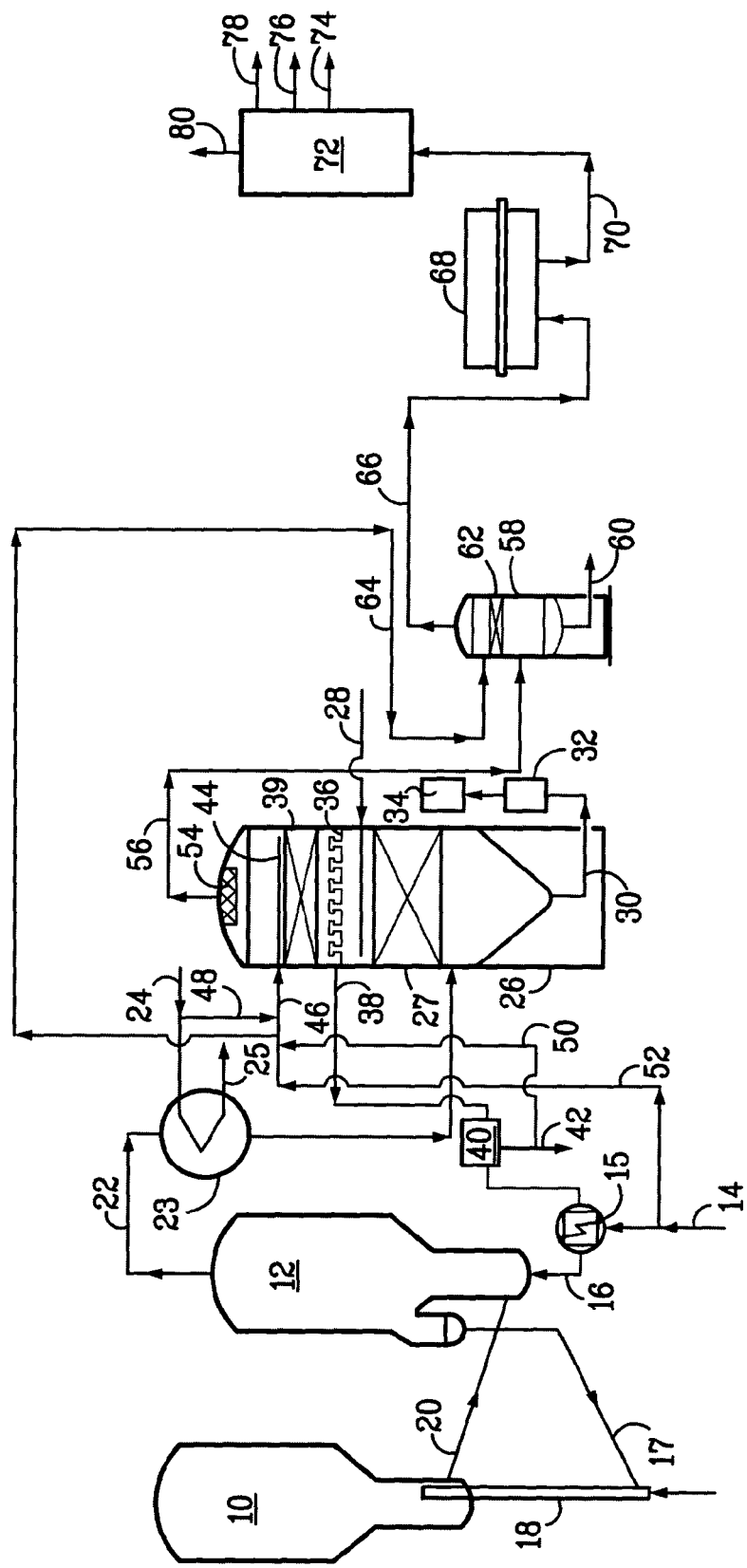

LIQUID CONTACTING OF POST-QUENCH EFFLUENT VAPOR STREAMS FROM OXYGENATE TO OLEFINS CONVERSION TO CAPTURE CATALYST FINES

FIELD

The present invention relates to treatment of product streams from processes utilizing fluidized catalyst, such as oxygenate-to-olefin processes (e.g., MTO), etc.

BACKGROUND

Olefins are traditionally produced from petroleum feedstocks by catalytic or steam cracking processes. These cracking processes, especially steam cracking, produce light olefin(s), such as ethylene and/or propylene, from a variety of hydrocarbon feedstocks. Ethylene and propylene are important commodity petrochemicals useful in a variety of processes for making plastics and other chemical compounds.

The petrochemical industry has known for some time that oxygenates, especially alcohols, are convertible into light olefin(s). There are numerous technologies available for producing oxygenates including fermentation or reaction of synthesis gas derived from natural gas, petroleum liquids or carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Other known syngas production processes include conventional steam reforming, autothermal reforming, or a combination thereof.

An important type of alternate feed for the production of light olefins is oxygenate, such as, for example, alcohols, particularly methanol and ethanol, dimethyl ether (DME), methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production. Methanol, the preferred alcohol for light olefin production, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor. The preferred process for converting a feedstock containing methanol into one or more olefin(s), primarily ethylene and/or propylene, involves contacting the feedstock with a catalyst composition.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the life and selectivity of the catalysts to ethylene and/or propylene.

Catalytic processes utilizing fluidized bed technology for conversion of hydrocarbon or oxygenates involving gas-solids contacting are widely used in industry for productions of petroleum-based fuels, chemical feed stocks and other industrial materials. The gaseous reactants are contacted with solid catalyst particles to provide gaseous products. Such processes often use continuous catalytic reactor unit operations, requiring catalyst regeneration at high temperature. FCC, MTO and other processes usually employ oxidative regeneration to remove coke or other carbonaceous deposits from spent or equilibrium catalysts. These operations often utilize combustion air to burn carbonaceous matter deposited on the catalyst during the conversion reactions. Ordinarily, this regeneration is carried out in a regeneration vessel separate from the main fluidized bed reactor. Attrition of the catalyst particles can occur during circulation of the catalyst into smaller particles of, say, less than about 60 microns, in overall diameter, i.e., the largest particle dimension.

The vaporous product from the reactor typically contains entrained particles such as catalyst fines carried from the process. Removal of such particles is desirable inasmuch as these particles can cause erosion and plugging problems for downstream equipment, e.g., suction drums, compressors, pumps, valves, exchangers and piping. Ultimately, the particles may be vented with gases to ambient atmosphere for disposal, e.g., through a cyclone used to separate solids from gases. Accordingly, it would be desirable to provide an economical method to reduce or substantially eliminate solids such as catalyst fines from the product effluent at a point upstream of equipment that can be damaged by such solids.

U.S. Pat. No. 6,121,504 to Kuechler et al. discloses a process for converting oxygenates to olefins with direct product quenching for heat recovery and to improve heat integration.

U.S. Pat. Nos. 6,403,854 and 6,459,009 to Miller et al. disclose a process for converting oxygenate to light olefins with improved heat recovery from reactor effluent streams and improved waste recovery which minimizes overall utility requirements. The reactor effluent is quenched with an aqueous stream in a two-stage process to facilitate the separation of hydrocarbon gases from any entrained catalyst fines, as well as to remove water and any heavy by-products such as $C_6+$ hydrocarbons. A portion of the waste water stream withdrawn from the bottom of the quench tower is recycled to the quench tower at a point above where the reactor effluent is introduced to the quench tower. The references do not appear to teach the use of liquid streams that are substantially free of catalyst fines for treating reactor effluents.

All of the above references are incorporated herein by reference in their entirety.

SUMMARY

In one aspect, the invention relates to a process for converting oxygenate to olefins which comprises: contacting a feedstock comprising oxygenate with a catalyst comprising a molecular sieve under conditions effective to produce a deactivated catalyst having carbonaceous deposits and a product comprising the olefins; separating the deactivated catalyst from the product to provide a separated vaporous product which contains catalyst fines; quenching the separated vaporous product with a liquid medium containing water and catalyst fines, in an amount sufficient for forming a light product fraction comprising light olefins and catalyst fines and a heavy product fraction comprising water, heavier hydrocarbons and catalyst fines; treating the light product fraction by contacting with a liquid oxygenate substantially free of catalyst fines to provide a light product fraction having reduced catalyst fines content and a liquid fraction of increased fines content; compressing the light product fraction having reduced catalyst fines content; and recovering the light olefins from the compressed light product fraction.

In one embodiment of this aspect of the invention, the liquid oxygenate substantially free of catalyst fines is selected from the group consisting of methanol and ethanol.

In another embodiment, the liquid oxygenate substantially free of catalyst fines is at least a portion of the feedstock comprising oxygenate. The feedstock comprising oxygenate can be heated by the treating.

In still another embodiment, the heated feedstock comprising oxygenate is contacted with the catalyst comprising a molecular sieve, i.e., the heated feedstock is cycled to a reactor wherein oxygenate is converted to olefins.

In yet another embodiment, the liquid oxygenate substantially free of catalyst fines is by-product water from the contacting of the oxygenate with the catalyst, which by-product water is condensed in a recovery unit and treated to reduce catalyst fines content.

In still another embodiment, the liquid oxygenate substantially free of catalyst fines is taken from boiler feed water used to make steam.

In still yet another embodiment, the liquid medium containing water is derived from quench tower bottoms. The quench tower bottoms can be passed through at least one of a quench heat exchange step and a water-methanol separation step before being cycled to the quench tower.

In yet another embodiment, the quenching takes place in a quench tower wherein the liquid medium containing water is introduced above where the separated vaporous product is introduced, and the treating of the light product fraction by contacting with a liquid oxygenate substantially free of catalyst fines occurs within the quench tower above where the liquid medium containing water is introduced.

In yet still another embodiment, a liquid draw device is placed above where the liquid medium containing water is introduced, from which liquid draw device the liquid fraction of increased fines content is taken; and the liquid oxygenate substantially free of catalyst fines is introduced at a point above the liquid draw device. Suitable liquid draw devices for use in the present invention include draw trays or draw pans, such as chimney trays. A chimney tray typically consists of a flat, solid piece of metal connected to a standard downcomer and containing chimneys or vertically hollow structures that convey the vapors upward through the tray.

In another embodiment, a vapor-liquid contacting surface is placed between the liquid draw device and where the liquid oxygenate substantially free of catalyst fines is introduced. Any suitable vapor-liquid contacting surface can be used, e.g., one provided by at least one material selected from the group consisting of random packing, structured packing and trays, as are well known to those of skill in the art.

In yet another embodiment, a demisting device is placed above where the liquid oxygenate substantially free of catalyst fines is introduced.

In still another embodiment, the quenching takes place in a quench tower wherein the liquid medium containing water is introduced above where the separated vaporous product is introduced, and the treating of the light product fraction occurs downstream of the quench tower.

In still yet another embodiment, the quenching takes place in a quench tower and the treating of the light product fraction at least partially occurs downstream in a suction drum.

In yet another embodiment, the quenching takes place in a quench tower and the treating of the light product fraction at least partially occurs downstream of the quench tower in a first stage suction drum. Typically, a vaporous effluent from the quench tower is directed to a suction drum intake from which liquid is removed below the intake and a vaporous overhead taken from the top of the suction drum, which is directed to the compressing step. The liquid oxygenate substantially free of catalyst fines is typically introduced to the suction drum above the suction drum intake. The liquid oxygenate substantially free of catalyst fines can be selected from the group consisting of methanol and ethanol. The liquid oxygenate substantially free of catalyst fines in one embodiment is at least a portion of the feedstock comprising oxygenate.

In another embodiment, the liquid oxygenate substantially free of catalyst fines is by-product water from the contacting of the oxygenate with the catalyst, which by-product water is condensed in a recovery unit and treated to reduce catalyst fines content.

In still another embodiment, the liquid oxygenate substantially free of catalyst fines is boiler feed water used to make steam.

In yet another embodiment, a vapor-liquid contacting surface is placed between where the liquid oxygenate substantially free of catalyst fines is introduced to the suction drum and the suction drum intake. The vapor-liquid contacting surface can be any suitable material providing sufficient surface area. Such vapor-liquid contacting surface can be provided by at least one material selected from the group consisting of random packing, structured packing and trays, which are well known to those of skill in the art.

In one embodiment of this aspect of the present invention, the process utilizes a catalyst comprising molecular sieve selected from the group consisting of ALPO-18, ALPO-34, SAPO-17, SAPO-18, SAPO-34, and SAPO-44, as well as substituted groups thereof. The molecular sieve is preferably SAPO-34.

In another embodiment of this aspect of the invention, the liquid medium containing water and catalyst fines contains at least about 0.01 wt % catalyst fines and the liquid oxygenate substantially free of catalyst fines contains less than about 0.01 wt % catalyst fines.

In still another embodiment, the liquid medium containing water and catalyst fines contains at least about 0.001 wt % catalyst fines and the liquid oxygenate substantially free of catalyst fines contains less than about 0.001 wt % catalyst fines.

In yet another embodiment, the liquid medium containing water and catalyst fines contains at least about 0.0001 wt % catalyst fines, e.g., at least about 0.00005 wt %, and the liquid oxygenate substantially free of catalyst fines contains less than about 0.0001 wt % catalyst fines, e.g., less than about 0.00005 wt % catalyst fines.

In another aspect, the present invention relates to an apparatus for converting oxygenates to olefins which comprises: a fluidized bed reactor for contacting a feedstock comprising oxygenate with a catalyst comprising a molecular sieve under conditions effective to produce a deactivated catalyst having carbonaceous deposits and a product comprising the olefins; a separator for separating the deactivated catalyst from the product to provide a separated vaporous product which contains catalyst fines; a quench tower for quenching the separated vaporous product with a liquid medium containing water and catalyst fines, in an amount sufficient for forming a light product fraction comprising light olefins and catalyst fines and a heavy product fraction comprising water, heavier hydrocarbons and catalyst fines; a treater for treating the light product fraction by contacting with a liquid oxygenate substantially free of catalyst fines to provide a light product fraction having reduced catalyst fines content and a liquid fraction of increased fines content; a compressor for compressing the light product fraction having reduced catalyst fines content; and a recovery train for recovering the light olefins from the compressed light product fraction.

In one embodiment, the apparatus further comprises: a line to recycle at least a portion of the liquid fraction of increased fines content to the reactor.

In another embodiment, the apparatus further comprises: a recovery unit for condensing by-product water from the reactor and a treater to at least partially remove catalyst fines from the condensed by-product water.

In still another embodiment, the apparatus further comprises: a steam boiler having a source of boiler feed water which can also be used as a source of the liquid oxygenate substantially free of catalyst fines.

In yet another embodiment, the apparatus further comprises: a line to recycle at least a portion of the heavy product fraction comprising water, heavier hydrocarbons and catalyst fines to the quench tower as the liquid medium containing water and catalyst fines. The line can further comprise at least one of a heat exchanger to remove heat from the heavy product fraction and a stripper to strip oxygenate from the heavy product fraction.

In still yet another embodiment, the quench tower of the apparatus comprises in ascending order: an inlet for introducing the separated vaporous product; an inlet for introducing the liquid medium containing water; and the treater.

In another embodiment, the treater of the apparatus comprises a liquid draw device having an outlet from which the liquid fraction of increased fines content is taken; and the quench tower of the apparatus comprises an inlet above the liquid draw device for introducing the liquid oxygenate substantially free of catalyst fines. The liquid draw device can be any suitable device known to those skilled in the art, e.g., a chimney tray.

In yet another embodiment, the apparatus comprises a vapor-liquid contacting surface placed between the liquid draw device and the inlet for introducing the liquid oxygenate substantially free of catalyst fines. The vapor-liquid contacting surface is provided by any suitable material, e.g., at least one material selected from the group consisting of random packing, structured packing and trays.

In still another embodiment, the apparatus comprises a demisting device placed above the inlet for introducing the liquid oxygenate substantially free of catalyst fines.

In still yet another embodiment, the apparatus comprises the treater located downstream from the quench tower.

In another embodiment, the apparatus further comprises a suction drum located between the quench tower and the compressor.

In yet another embodiment, the suction drum of the apparatus comprises a treater for treating the light product fraction by contacting with a liquid oxygenate substantially free of catalyst fines to provide a light product fraction having reduced catalyst fines content and a liquid fraction of increased fines content. The suction drum can be a first stage suction drum.

In still another embodiment, the suction drum of the apparatus comprises: an intake for receiving vaporous effluent from the quench tower; a lower outlet from which liquid is removed; and an overhead outlet from which a vaporous overhead is taken for the compressor.

In still yet another embodiment, the suction drum of the apparatus comprises an inlet for introducing the liquid oxygenate substantially free of catalyst fines above the suction drum intake. The inlet for introducing the liquid oxygenate substantially free of catalyst fines can be connected to a treater for reducing catalyst fines content supplied by a recovery unit that condenses by-product water taken from the reactor.

In another embodiment, the apparatus further comprises a boiler for making steam and the inlet for introducing the liquid oxygenate substantially free of catalyst fines is connected to a source of boiler feed water for the boiler.

In yet another embodiment, the apparatus further comprises a vapor-liquid contacting surface placed between the inlet for introducing the liquid oxygenate substantially free of catalyst fines to the suction drum and the suction drum intake. The vapor-liquid contacting surface is provided by at least one material selected from the group consisting of random packing, structured packing and trays.

DESCRIPTION OF THE DRAWINGS

The FIGURE is a schematic process flow diagram depicting certain aspects of the invention.

DETAILED DESCRIPTION

Molecular Sieves and Catalysts Thereof for Use in OTO Conversion

Molecular sieves suited to use for converting oxygenates to olefins (OTO) have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types,* 5th edition, Elsevier, London, England (2001), which is herein fully incorporated by reference.

Non-limiting examples of these molecular sieves are the small pore molecular sieves of a framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves of a framework-type selected from the group consisting of AFO, AEL, EUO, HEU, FER, MEL, MFI, MTW, MTT, TON, and substituted forms thereof; and the large pore molecular sieves of a framework-type selected from the group consisting of EMT, FAU, and substituted forms thereof. Other molecular sieves have a framework-type selected from the group consisting of ANA, BEA, CFI, CLO, DON, GIS, LTL, MER, MOR, MWW and SOD. Non-limiting examples of the preferred molecular sieves, particularly for converting an oxygenate containing feedstock into olefin(s), include those having a framework-type selected from the group consisting of AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing TO$_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B.V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves utilized in the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing [TO$_4$] tetrahedral units, more preferably, two or more [SiO$_4$], [AlO$_4$] and/or [PO$_4$] tetrahedral units, and most preferably [SiO$_4$], [AlO$_4$] and [PO$_4$] tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

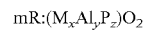

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIIB, VIIB, VIIIB and Lanthanides of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

The molecular sieves useful for oxygenates to olefins conversion processes are synthesized and then made or formulated into catalysts by combining the synthesized molecular sieves with a binder and/or a matrix material to form a molecular sieve catalyst composition. This molecular sieve catalyst composition is formed into useful shaped and sized particles by well-known techniques such as spray drying, pelletizing, extrusion, and the like.

Oxygenate to Olefins Process

In a preferred embodiment of an oxygenate to olefins process, the feedstock contains one or more oxygenates, more specifically, one or more organic compound(s) containing at least one oxygen atom. In the most preferred embodiment, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in an oxygenate to olefins process include lower straight and branched chain aliphatic alcohols and their unsaturated counterparts.

Non-limiting examples of suitable oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or in combination, are converted from a feedstock containing an oxygenate, preferably an alcohol, most preferably methanol, to the preferred olefin(s) ethylene and/or propylene.

There are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 85 weight percent.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see, for example, U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in, for example, U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613, filed May 4, 2000 (multiple riser reactor), which are all herein fully incorporated by reference.

In a preferred embodiment, a fluidized bed process or high velocity fluidized bed process includes a reactor system, a regeneration system and a recovery system.

The reactor system preferably is a fluid bed reactor system having a first reaction zone within one or more riser reactor(s) within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol.

Treatment of the oxygenate-containing feedstock prior to its introduction to the oxygenate to olefins conversion reactor may be required to remove non-volatile contaminants.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 hr$^{-1}$ to about 20,000 hr$^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 hr$^{-1}$ to about 5000 hr$^{-1}$, preferably from about 2 hr$^{-1}$ to about 3000 hr$^{-1}$, more preferably from about 5 hr$^{-1}$ to about 1500 hr$^{-1}$, and most preferably from about 10 hr$^{-1}$ to about 1000 hr$^{-1}$. In one preferred embodiment, the WHSV is greater than 20 hr$^{-1}$, preferably the WHSV for conversion of a feedstock containing methanol and dimethyl ether is in the range of from about 20 hr$^{-1}$ to about 300 hr$^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec, e.g., greater than about 15 m/sec. See, for example, U.S. Pat. No. 6,552,240 to Lattner et al., which is herein incorporated by reference.

In one preferred embodiment of the process for converting an oxygenate to olefin(s) using a silicoaluminophosphate molecular sieve catalyst composition, the process is operated at a WHSV of at least 20 hr$^{-1}$ and a Temperature Corrected Normalized Methane Selectivity (TCNMS) of less than 0.016, preferably less than or equal to 0.01. See, for example, U.S. Pat. No. 5,952,538, which is herein fully incorporated by reference.

In another embodiment of the process for converting an oxygenate such as methanol to one or more olefin(s) using a molecular sieve catalyst composition, the WHSV is from 0.01 hr$^{-1}$ to about 100 hr$^{-1}$, at a temperature of from about 350° C. to 550° C., and silica to Me$_2$O$_3$ (Me is selected from Group 13 (IIIA), Groups 8, 9 and 10 (VIII) elements) from the Periodic Table of Elements), and a molar ratio of from 300 to 2500. See, for example, EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, $NO$, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration is in the range of from about 10 psia (68 kPaa) to about 500 psia (3448 kPaa), preferably from about 15 psia (103 kPaa) to about 250 psia (1724 kPaa), and more preferably from about 20 psia (138 kPaa) to about 150 psia (1034 kPaa). Typically, the pressure is less than about 60 psia (414 kPaa).

The preferred residence time of the molecular sieve catalyst composition in the regenerator is in the range of from about one minute to several hours, most preferably about one minute to 100 minutes, and the preferred volume of oxygen in the flue gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The gaseous effluent from the OTO reactor is withdrawn from the disengaging system and is passed through a recovery system. There are many well-known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, for reaction systems such as ethylbenzene manufacture (U.S. Pat. No. 5,476,978) and other derivative processes such as aldehydes, ketones and ester manufacture (U.S. Pat. No. 5,675,041), and other associated equipment, for example, various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene ($C_2$) splitter, propylene ($C_3$) splitter, butene ($C_4$) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

The reaction products that are withdrawn from the OTO reactor advantageously can be cooled and separated from water, a by-product of the conversion, in a quench tower before the olefin products are recovered. In the quench tower, most of the water is condensed and the light hydrocarbons and light oxygenates removed from the top of the quench tower as an overhead stream and the water removed from the bottom of the quench tower. Water removed from the quench tower comprises some dissolved light hydrocarbons and heavy by-products including heavy oxygenates, e.g., alcohols and ketones, which have a normal boiling point greater than or equal to water and which can be removed by stripping the water from heavy by-products with light gases such as steam or nitrogen. The feedstream passed to an OTO reactor can be refined methanol (essentially pure), or raw methanol comprising up to about 30 weight percent water. The feedstream is advantageously heated and vaporized prior to being charged to the fluidized bed OTO reactor, which requires a considerable amount of energy. Therefore, it is necessary to recover as much as energy of the reactor effluent and use it to heat and vaporize the feedstream. However, water is substantially the only condensation product in the quench tower. The reaction zone can comprise either a fixed bed or a fluidized reaction zone, but a fluidized reaction zone is preferred.

In the operation of conventional quench systems, essentially all of the water withdrawn from the bottom of the quench tower is contaminated and must undergo further treatment before it can be returned to the process as pumparound. The pumparound can be cooled by indirect heat exchange with the feedstream. Even after decontamination treatment, the pumparound or recycled water typically contains substantial amounts of fines, which results in a quench tower overhead containing catalyst fines in amounts deleterious to downstream installations, particularly suction drums and compressors, e.g., the first stage suction drum and the first stage compressor which are typically found in the recovery train.

The present invention treats quench overhead effluent streams by employing a vapor-liquid contact zone upstream of these downstream installations, particularly upstream of the first stage compressor, e.g., upstream of or at the first stage suction drum. In one embodiment the treating takes place within the quench tower enclosure above where the quench water is introduced, i.e., the vapor-liquid contact zone is positioned upstream of the introduction site for quench water.

The vapor-liquid contact zone employed within the quench tower enclosure typically includes an optional liquid draw device such as a chimney tray, from which liquid such as water and/or oxygenate, e.g., methanol, can be drawn off. The drawn off liquid, if it contains water in excess to that permissible in an oxygenate feed to the reactor, can be passed to a water-methanol separation means, e.g., a stripper, as necessary. The liquid (after stripping if necessary) is passed to the oxygenate to olefins conversion reactor as feed (via a feed vaporizer as necessary).

Above the liquid draw device (or above or downstream of the quench water inlet where no liquid draw device is used) can be placed suitable materials providing solid surfaces for contacting the vaporous quench overhead effluent, e.g., trays or a packing material that facilitates intimate gas/liquid contact. The gas/liquid contacting material may include, but is not limited to random packing, structured packing and/or trays. Examples of these include, Gauze, Ripple Trays, Sieve trays, cross-flow sieve, valve, or bubble cap trays, structured packings such as Metal Max Pak® Mellapak®, Flexipac®, Gempak®, Goodloe®, Sulzer®, or random or dumped packing, such as berl saddles, Intalox® saddles, raschig rings, Pall® rings, and Nutter Rings™. These and other types of suitable gas/liquid contacting equipment are described in detail in Kister, H. Z. Distillation Design, McGraw-Hill, N.Y. (1992), Chapters 6 and 8, the disclosures of which are incorporated herein by reference. Typically such materials are packed to a depth ranging from about 2 ft to about 40 ft (from about 0.6 m to about 12 m), say, from about 4 ft to about 20 ft (from about 1.2 m to about 6 m). A vapor-liquid contact zone can be provided downstream of the quench tower enclosure in a separate enclosure upstream of the first stage compressor in the recovery train. Such a vapor-liquid contact zone can be provided in addition to the one in the quench tower enclosure, or alternately in place of the vapor-liquid contact zone in the quench tower enclosure. Typically, a vapor-liquid contact zone downstream of the quench tower can be placed in a dedicated enclosure, or alternately within a suction drum.

A liquid substantially free of catalyst fines is introduced at a point above (or downstream of) the trays or packing materials in the vapor-liquid contact zone(s).

The overhead from the quench step, which typically contains at least about 0.0001 wt %, e.g., at least about 0.001 wt %, say, at least about 0.01 wt %, e.g., from about 0.0001 to about 0.05 wt % of catalyst fines whose overall particle diameter is less than about 60 microns, say, from about 5 to about 50 microns, e.g., from about 10 to about 30 microns, passes through a vapor-liquid contact zone. The vapor-liquid contacting zone comprises an inlet for introducing a liquid which is substantially free of fines of overall diameter of less than about 60 microns, e.g., from about 5 to about 50 microns, say, from about 10 to about 30 microns. The liquid substantially free of catalyst fines contains a concentration of catalyst fines lower than the overhead from the quench step, such that the vapor-liquid contacting provides a liquid fraction having increased catalyst fines content relative to the liquid substantially free of catalyst fines and an overhead or gaseous effluent fraction having decreased catalyst fines content relative to the overhead from the quench step. The catalyst fines content of the overhead from the quench step can vary depending on the efficiency of upstream cyclones utilized, e.g., in the catalyst regenerator, as well as upon the catalyst fines content of quench water recycled from the bottoms of the quench tower that contain catalyst fines. The fines content can be dependent on the effectiveness of treatment, if any, of the bottoms prior to their reintroduction to the quench tower, as well as the relative amounts of newly added quench water which is free of catalyst fines with recycled sources. Such treatments can include quench water separation treatment, e.g., water-methanol separation, e.g., in a stripper.

The liquid substantially free of catalyst fines typically contains less than about 0.01 wt % catalyst fines (wherein the catalyst fines have an overall diameter of less than about 60 microns, say, from about 5 to about 50 microns), e.g., less than about 0.001 wt % catalyst fines, say, less than about 0.0001 wt % or even less than about 0.00001 wt % of catalyst fines, e.g., ranging from about 0.000005 wt % to about 0.005 wt % of catalyst fines. Such liquid can be obtained from any suitable source providing a liquid of low or no catalyst fines content. Examples include sources of oxygenate, e.g., methanol, and water or mixtures thereof which meet the catalyst fines content requirement either in their original state or as treated to at least partially remove catalyst fines. Suitable sources include the oxygenate feed for the oxygenate to olefins reactor, which may contain oxygenate alone or oxygenate, e.g., methanol, mixed with water. Other sources include water obtained from a stripper, which water has been filtered or otherwise treated to meet the requisite catalyst fines content. Sources of boiler feed water suitable as feed for steam boilers are also desirable sources of such liquids substantially free of catalyst fines, given their low or non-existent catalyst fines content.

Such sources of liquid substantially free of catalyst fines can be treated to remove or add heat as necessary by heat exchange with other streams of the oxygenates to olefins conversion process or by any other suitable means such as direct heating or cryogenic treatment, e.g., in a heat exchanger used to treat quench tower bottoms. Typically, the liquid substantially free of catalyst fines is cooler than the quench overhead it is used to treat, say, at least about 2° C., e.g., at least 10° C. or even at least about 15° C. cooler, typically from about 2° to about 10° C. cooler. Temperatures of such liquid can range from about 2° to about 8° C., e.g., from about 3° to about 5° C.

The present invention by providing additional treatment to quench overhead using liquid substantially free of catalyst fines, reduces erosion on downstream equipment while in certain instances providing additional heat to oxygenate-containing feeds to the reactor.

Referring to the FIGURE, the method and apparatus of the present invention are depicted in a schematic process flow sheet. Regenerator vessel 10, in which can be placed cyclones to at least partially remove catalyst fines, is operatively connected to reactor vessel 12 which is fed an oxygenated feed via line 14 which can be vaporized in feed vaporizer 15 prior to introduction to the reactor vessel 12 via line 16. Depleted catalyst is removed via line 17 to the regenerator 10 to regenerator catalyst inlet 18. Regenerated catalyst is taken from the regenerator via line 20 to the bottom of the reactor vessel 12. Vaporous catalyst fines-containing product effluent is removed from the reactor via line 22 and directly or indirectly (via heat exchanger 23 which utilizes boiler feed water fed via line 24 to make steam taken from line 25) introduced to quench tower 26 where it moves upwardly and contacts in a vapor-liquid contacting zone 27 a downwardly passing liquid containing water and catalyst fines introduced via line 28 which may be fed by a stream derived from quench tower bottoms taken from line 30 containing water, oxygenate, e.g., methanol and catalyst fines. The stream from the quench tower bottoms can be optionally heat exchanged in heat exchanger 32 and optionally stripped, e.g., in a water-methanol separator 34, prior to being directed to line 28. The quenched overhead which can contain problematic amounts of catalyst fines is passed to a treating zone where it undergoes additional vapor-liquid contacting in a second vapor-liquid contacting zone at a point upstream of compressor 68, this time with a liquid which is substantially free of catalyst fines, providing a vaporous overhead of significantly reduced catalyst fines content. In one embodiment, the vapor-liquid contacting zone is present in the enclosure of the quench tower itself. In this instance the second vapor-liquid contacting zone includes a liquid draw device such as chimney tray 36 wherein quench overhead passes via chimney inlets and from which can be drawn off liquid collected in the tray via line 38. The thus drawn off liquid contains catalyst fines taken from the quench tower overhead, and if containing water in excess of what is suitable for an oxygenate to olefins conversion reactor feed, can be conveyed to a stripper 40 (from which water is taken off via line 42) prior to being conveyed to feed vaporizer 15 and thence introduced to the reactor vessel 12 via line 16.

Positioned above chimney tray 36 is a bed 39 providing surface area for vapor-liquid contacting, which bed can comprise trays or suitable irregular or regular packing as is known to those of skill in the art. Above the bed is an inlet for introducing liquid substantially free of catalyst fines via a liquid distributor 44 fed from line 46 which in turn can be fed by one or more suitable sources of liquid substantially free of catalyst fines. Such sources include boiler feed water fed via line 48, stripped water from an oxygenate-water stripper via line 50 or unvaporized oxygenate feed via line 52. The treated overhead from which catalyst fines have been removed by contacting with the liquid substantially free of catalyst fines passes out of a demister 54 located at the top of the quench tower enclosure which collects entrained liquid. The quenched and treated overhead which contains low amounts of catalyst fines conveyed via line 56 to the recovery train which may include an optional first stage suction drum 58 which removes any additional liquid formed in the quenched and treated overhead via line 60 prior to a compression step. The overhead can be passed directly to the compression step (if it has already passed to a post-quench treater as described above) or through a second (or third) vapor-liquid contacting zone configured as described above with respect to the quench tower enclosure except for lacking a chimney tray, liquid (and catalyst fines) being drawn off via line 60. This vapor-liquid contacting zone can be either a substitute for or, in addition to the vapor-liquid contacting zone associated with the quench tower. The liquid substantially free of catalyst fines is introduced to the suction drum 58 via line 64 which can be fed by any suitable source, including line 46 which in turn is fed by any of lines 48, 50, and 52. Treated or untreated overhead from the suction drum 58 is taken via line 66 where it is directly or indirectly conveyed to a first stage compressor 68. The compressed overhead from the suction drum is conveyed via line 70 to a recovery train 72 providing recovered products via lines 74, 76, 78 and 80.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A process for converting oxygenate to olefins which comprises:
    contacting a feedstock comprising oxygenate with a catalyst comprising a molecular sieve under conditions effective to produce a deactivated catalyst having carbonaceous deposits and a product comprising said olefins;
    separating said deactivated catalyst from said product to provide a separated vaporous product which contains catalyst fines;
    quenching said separated vaporous product with a liquid medium containing water and catalyst fines, in an amount sufficient for forming a light product fraction comprising light olefins and catalyst fines and a heavy product fraction comprising water, heavier hydrocarbons and catalyst fines;
    treating said light product fraction by contacting with a liquid oxygenate substantially free of catalyst fines to provide a light product fraction having reduced catalyst fines content and a liquid fraction of increased fines content, said liquid oxygenate substantially free of catalyst fines being selected from the group consisting of methanol and ethanol;
    compressing said light product fraction having reduced catalyst fines content; and
    recovering said light olefins from said compressed light product fraction.

2. The process of claim 1 wherein said liquid oxygenate substantially free of catalyst fines is methanol.

3. The process of claim 1 wherein said liquid oxygenate substantially free of catalyst fines is at least a portion of said feedstock comprising oxygenate.

4. The process of claim 3 wherein said feedstock comprising oxygenate is heated by said treating.

5. The process of claim 4 wherein said heated feedstock comprising oxygenate is contacted with said catalyst comprising a molecular sieve.

6. The process of claim 1 wherein said liquid oxygenate substantially free of catalyst fines is contained in by-product water from said contacting of the oxygenate with said catalyst, which by-product water is condensed in a recovery unit and treated to reduce catalyst fines content.

7. The process of claim 1 wherein said oxygenate comprises methanol.

8. The process of claim 1 wherein said liquid medium containing water is derived from quench tower bottoms.

9. The process of claim 8 wherein said quench tower bottoms are passed through at least one of a quench heat exchange step and a water-methanol separation step before being cycled to said quench tower.

10. The process of claim 1 wherein said quenching takes place in a quench tower wherein said liquid medium containing water is introduced above where said separated vaporous product is introduced, and said treating of said light product fraction by contacting with a liquid oxygenate substantially free of catalyst fines occurs within the quench tower above where said liquid medium containing water is introduced.

11. The process of claim 10 wherein a liquid draw device is placed above where the liquid medium containing water is introduced, from which liquid draw device said liquid fraction of increased fines content is taken; and said liquid oxygenate substantially free of catalyst fines is introduced at a point above said liquid draw device.

12. The process of claim 10 wherein said liquid draw device is a chimney tray.

13. The process of claim 11 wherein a vapor-liquid contacting surface is placed between said liquid draw device and where said liquid oxygenate substantially free of catalyst fines is introduced.

14. The process of claim 13 wherein said vapor-liquid contacting surface is provided by at least one material selected from the group consisting of random packing, structured packing and trays.

15. The process of claim 14 wherein a demisting device is placed above where said liquid oxygenate substantially free of catalyst fines is introduced.

16. The process of claim 1 wherein said quenching takes place in a quench tower wherein said liquid medium containing water is introduced above where said separated vaporous product is introduced, and said treating of said light product fraction occurs downstream of said quench tower.

17. The process of claim 1 wherein said quenching takes place in a quench tower and said treating of said light product fraction at least partially occurs downstream in a suction drum.

18. The process of claim 1 wherein said quenching takes place in a quench tower and said treating of said light product fraction at least partially occurs downstream of said quench tower in a first stage suction drum.

19. The process of claim 17 wherein a vaporous effluent from said quench tower is directed to a suction drum intake from which liquid is removed below said intake and a vaporous overhead taken from the top of said suction drum which is directed to said compressing step.

20. The process of claim 19 wherein said liquid oxygenate substantially free of catalyst fines is introduced to said suction drum above said suction drum intake.

21. The process of claim 20 wherein said liquid oxygenate substantially free of catalyst fines is methanol.

22. The process of claim 20 wherein said liquid oxygenate substantially free of catalyst fines is at least a portion of said feedstock comprising oxygenate.

23. The process of claim 20 wherein said liquid oxygenate substantially free of catalyst fines is contained in by-product water from said contacting of the oxygenate with said catalyst, which by-product water is condensed in a recovery unit and treated to reduce catalyst fines content.

24. The process of claim 20 wherein said feedstock comprising oxygenate comprises methanol.

25. The process of claim 20 wherein a vapor-liquid contacting surface is placed between where said liquid oxygenate substantially free of catalyst fines is introduced to said suction drum and said suction drum intake.

26. The process of claim 25 wherein said vapor-liquid contacting surface is provided by at Least one material selected from the group consisting of random packing, structured packing and trays.

27. The process of claim 1 wherein said molecular sieve is selected from the group consisting of ALPO-18, ALPO-34, SAPO-17, SAPO-18, SAPO-34, and SAPO-44 and substituted groups thereof.

28. The process of claim 1 wherein said molecular sieve is SAPO-34.

29. The process of claim 1 wherein said liquid medium containing water and catalyst fines contains at least about 0.01 wt % catalyst fines and said liquid oxygenate substantially free of catalyst fines contains less than about 0.01 wt % catalyst fines.

30. The process of claim 1 wherein said liquid medium containing water and catalyst fines contains at least about 0.001 wt % catalyst fines and said liquid oxygenate substantially free of catalyst fines contains less than about 0.001 wt % catalyst fines.

31. The process of claim 1 wherein said liquid medium containing water and catalyst fines contains at least about 0.0001 wt % catalyst fines and said liquid oxygenate substantially free of catalyst fines contains less than about 0.0001 wt % catalyst fines.

* * * * *